(12) United States Patent
Suzuki et al.

(10) Patent No.: US 9,072,538 B2
(45) Date of Patent: Jul. 7, 2015

(54) TREATMENT TOOL FOR ENDOSCOPE

(75) Inventors: Keita Suzuki, Tokyo (JP); Megumi Kimura, Tokyo (JP); Kazuya Sato, Hirosaki (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 0 days.

(21) Appl. No.: 13/306,127

(22) Filed: Nov. 29, 2011

(65) Prior Publication Data
US 2012/0203063 A1    Aug. 9, 2012

Related U.S. Application Data
(63) Continuation of application No. PCT/JP2011/062468, filed on May 31, 2011.

(30) Foreign Application Priority Data

May 31, 2010 (JP) ................................ 2010-124664

(51) Int. Cl.
*A61B 17/00* (2006.01)
*A61D 1/12* (2006.01)
(Continued)

(52) U.S. Cl.
CPC ................ *A61B 17/29* (2013.01); *A61B 10/06* (2013.01); *A61B 17/2816* (2013.01);
(Continued)

(58) Field of Classification Search
CPC ................... A61B 17/29; A61B 10/06; A61B 2017/2946; A61B 2017/2941; A61B 17/2816; A61B 2017/2939; A61B 2017/2929; A61B 2017/2926; A61B 2017/2947; A61B 2017/2932
USPC ............. 606/205–209, 106, 51; 600/564–567
See application file for complete search history.

(56) References Cited

U.S. PATENT DOCUMENTS 4,721,116 A * 1/1988 Schintgen et al. ............ 600/564
(Continued)

FOREIGN PATENT DOCUMENTS

EP    0 712 608 A2    5/1996
(Continued)

OTHER PUBLICATIONS

European Search Report dated Oct. 29, 2012 from corresponding European Patent Application No. EP 11 78 9793.4.
(Continued)

*Primary Examiner* — Ashley Fishback
*Assistant Examiner* — Jing Ou
(74) *Attorney, Agent, or Firm* — Scully, Scott, Murphy & Presser, P.C.

(57) ABSTRACT

A treatment tool for endo scope includes a pair of forceps members (first forceps members and second forceps member) supported by a forceps rotation axis such that they can rotate relatively, an operation part for performing an open-close operation of the pair of forceps members, an operation wire that connects the pair of forceps members and the operation part, an insertion part which the operation wire is inserted into, a cover member that secures the forceps rotation axis to the insertion part, a connection member including a link rotation axis, provided at a distal-end part of the operation wire, and a pair of link members (first link member and second link member), first end parts of each being rotatably connected via respective rotation axis members to a proximal-end part of each of the pair of forceps members, and second end parts of each being rotatably connected to the link rotation member. The cover member includes grooves formed such that, by engaging with end parts of the rotation axis members, they restrict the movement of the rotation axis members in a direction of approaching the axis of the operation wire.

3 Claims, 9 Drawing Sheets

(51) Int. Cl.
*A61B 17/29* (2006.01)
*A61B 10/06* (2006.01)
*A61B 17/28* (2006.01)

(52) U.S. Cl.
CPC  *A61B 2017/2929* (2013.01); *A61B 2017/2939* (2013.01); *A61B 2017/2941* (2013.01); *A61B 2017/2946* (2013.01)

(56) References Cited

U.S. PATENT DOCUMENTS

| | | | | |
|---|---|---|---|---|
| 4,982,727 | A * | 1/1991 | Sato | 600/104 |
| 5,133,727 | A * | 7/1992 | Bales et al. | 606/170 |
| 5,152,778 | A * | 10/1992 | Bales et al. | 606/205 |
| 5,571,129 | A * | 11/1996 | Porter | 606/170 |
| 5,666,965 | A * | 9/1997 | Bales et al. | 600/562 |
| 5,695,521 | A * | 12/1997 | Anderhub | 606/205 |
| 5,722,421 | A * | 3/1998 | Francese et al. | 600/564 |
| 5,810,876 | A * | 9/1998 | Kelleher | 606/205 |
| 5,820,630 | A * | 10/1998 | Lind | 606/208 |
| 5,976,130 | A | 11/1999 | McBrayer et al. | |
| 6,063,103 | A | 5/2000 | Hashiguchi | |
| 6,964,662 | B2 * | 11/2005 | Kidooka | 606/52 |
| 7,014,649 | B2 * | 3/2006 | Bacher | 606/205 |
| 7,775,989 | B2 * | 8/2010 | Nakao | 600/564 |
| 2001/0025149 | A1 * | 9/2001 | Kobayashi et al. | 600/564 |
| 2001/0041912 | A1 * | 11/2001 | Ouchi | 606/205 |
| 2002/0123667 | A1 * | 9/2002 | Ouchi | 600/201 |
| 2004/0068291 | A1 * | 4/2004 | Suzuki | 606/205 |
| 2004/0186348 | A1 * | 9/2004 | Kidooka | 600/104 |
| 2004/0249411 | A1 * | 12/2004 | Suzuki | 606/205 |
| 2005/0049520 | A1 * | 3/2005 | Nakao | 600/562 |
| 2005/0222611 | A1 * | 10/2005 | Weitkamp | 606/205 |
| 2006/0189892 | A1 * | 8/2006 | Okada | 600/564 |
| 2006/0258954 | A1 | 11/2006 | Timberlake et al. | |
| 2008/0147113 | A1 * | 6/2008 | Nobis et al. | 606/205 |
| 2009/0299143 | A1 * | 12/2009 | Conlon et al. | 600/153 |
| 2010/0298864 | A1 * | 11/2010 | Castro | 606/205 |
| 2011/0196418 | A1 * | 8/2011 | Castro | 606/205 |

FOREIGN PATENT DOCUMENTS

| | | |
|---|---|---|
| EP | 1 994 904 A1 | 11/2008 |
| JP | 6-296619 A | 10/1994 |
| JP | 10-179602 A | 7/1998 |
| JP | 2003-299669 A | 10/2003 |
| JP | 2003-299670 A | 10/2003 |
| JP | 4197983 B2 | 10/2008 |

OTHER PUBLICATIONS

International Search Report PCT/JP2011/062468 dated Jun. 28, 2011.

English abstract only of Japanese Patent Application No. JP 2004-321660 published Nov. 18, 2004.

* cited by examiner

US 9,072,538 B2

TREATMENT TOOL FOR ENDOSCOPE

The present application claims priority on Application 2010-124664 filed in Japan on May 31, 2010, and is a continuing application based on International Patent Application PCT/JP2011/062468, filed on May 31, 2011, the contents of both these applications being incorporated herein.

BACKGROUND OF THE INVENTION

1. Field of the Invention

The present invention relates to a treatment tool for endoscope used by being inserted via an endoscope into a body cavity.

2. Description of Related Art

There is a conventionally known treatment tool for endoscope (hereinafter abbreviated as 'treatment tool') that is inserted via an endoscope into a body cavity and used for carrying out various types of treatment to a body cavity tissue of a patient or the like.

One example of a treatment tool is a forceps described in Japanese Patent Application No. 4197983. A pair of forceps members are provided at a distal end of the forceps, and are supported via a rotation axis such that they can rotate relative to each other.

An operation wire connects the pair of forceps members to an operation part at the holding side. Two link members are rotatably provided at the distal end of the operation wire. The distal ends of the link members are rotatably attached to the respective proximal ends of one and the other of the pair of forceps members.

With the configuration described above, when the operation wire is advanced and retracted in the axis direction via the operation part, the pair of forceps members opens and closes relatively around the rotation axis.

SUMMARY OF THE INVENTION

According to a first aspect of the invention, a treatment tool for endoscope includes a pair of forceps members supported by a forceps rotation axis such that they can rotate relatively, an operation part for performing an open-close operation of the pair of forceps members, an operation wire that connects the pair of forceps members and the operation part, an insertion part which the operation wire is inserted into, a cover member that secures the forceps rotation axis to the insertion part, a connection member including a link rotation member, provided at a distal-end part of the operation wire, and a pair of link members, first end parts of each being rotatably connected via respective rotation axis members to a proximal-end part of each of the pair of forceps members, and second end parts of each being rotatably connected to the link rotation member. The cover member includes restricting parts formed such that, by engaging with end parts of the rotation axis members, they restrict the movement of the rotation axis members in a direction of approaching the axis of the operation wire.

According to a second aspect of the invention, the restricting parts are provided in the cover member such that they open in a direction of separating from the axis of the operation wire.

According to a third aspect of the invention, the connection member includes two of the link rotation axes, and their axes are parallel with each other separating from the axis of the operation wire.

According to a fourth aspect of the invention, second end parts of the pair of link members are rotatably connected to each of two the link rotation axes, and, when the pair of forceps members are in the closed state, the link members are parallel to each other.

DETAILED DESCRIPTION OF THE INVENTION

A treatment tool for endoscope according to a first embodiment of the invention will be explained with reference to FIGS. 1 to 5.

Figure 1:
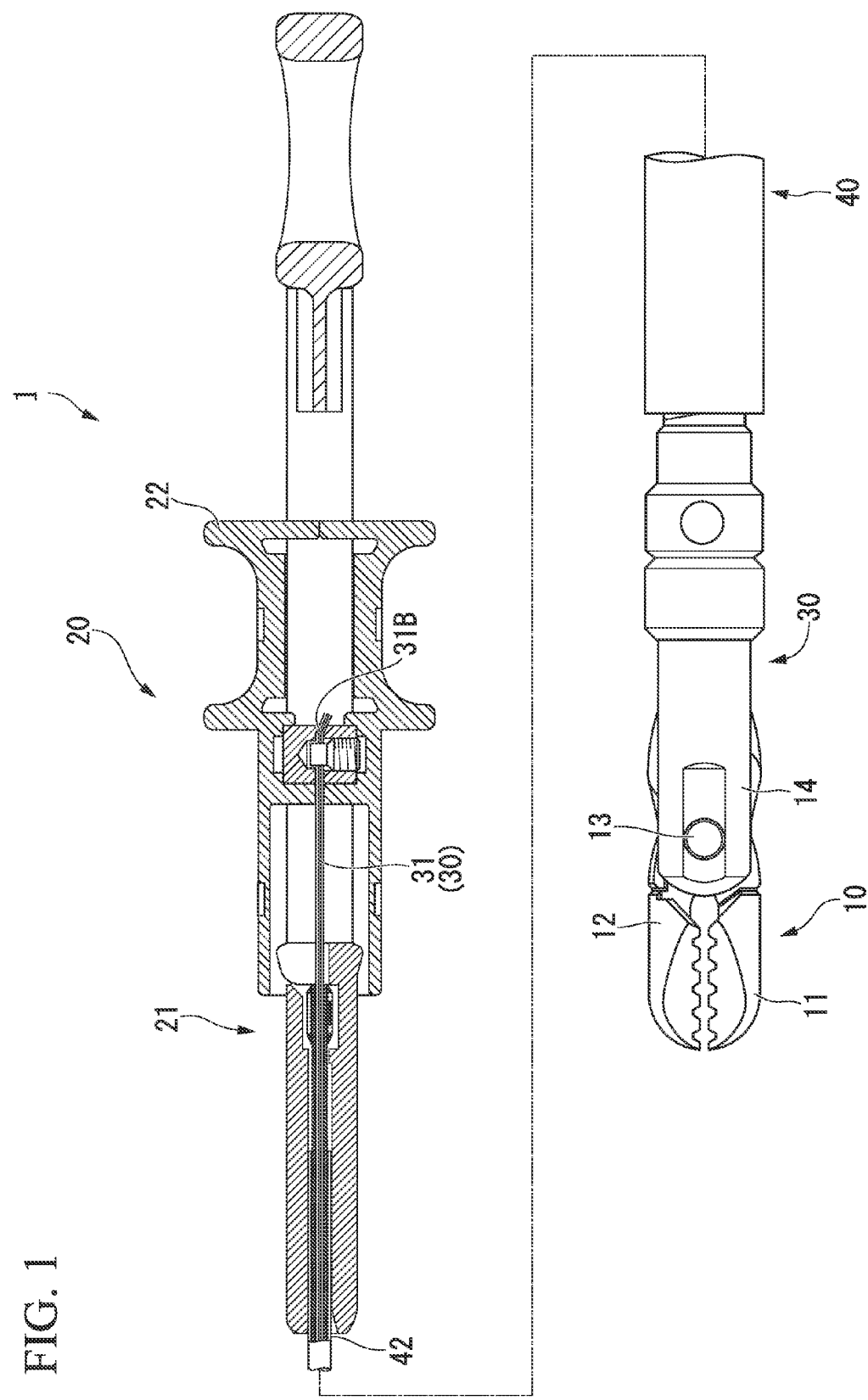
FIG. 1 is an overall diagram of a treatment tool for endoscope according to a first embodiment of the invention.

As shown in FIG. 1, a treatment tool 1, which is a treatment tool for endoscope according to this embodiment, includes a treatment part 10 for carrying out treatment to a body cavity tissue, an operation part 20 for operating the treatment part 10, a connection part 30 for connecting the treatment part 10 and the operation part 20, and an elongated insertion part 40 that is inserted into the body cavity.

In the treatment part, a pair of forceps members consisted of a first forceps member 11 and a second forceps member 12 are supported by a forceps rotation member 13 such that they can rotate relatively to each other. The forceps rotation member 13 is supported by a cover (cover member) 14 disposed such that it encloses the forceps members 11 and 12.

The operation part 20 includes a main unit 21 which the insertion part 40 is attached to, and a slider 22 attached to the main unit 21 such that it can slide. The slider 22 and the treatment part 10 are connected by the connection part 30. When the slider 22 slide in the long direction of the main unit 21, the pair of forceps members 11 and 12 opens and closes. This point will be explained in greater detail in the explanation of an operation when using the treatment tool 1.

Figure 2:
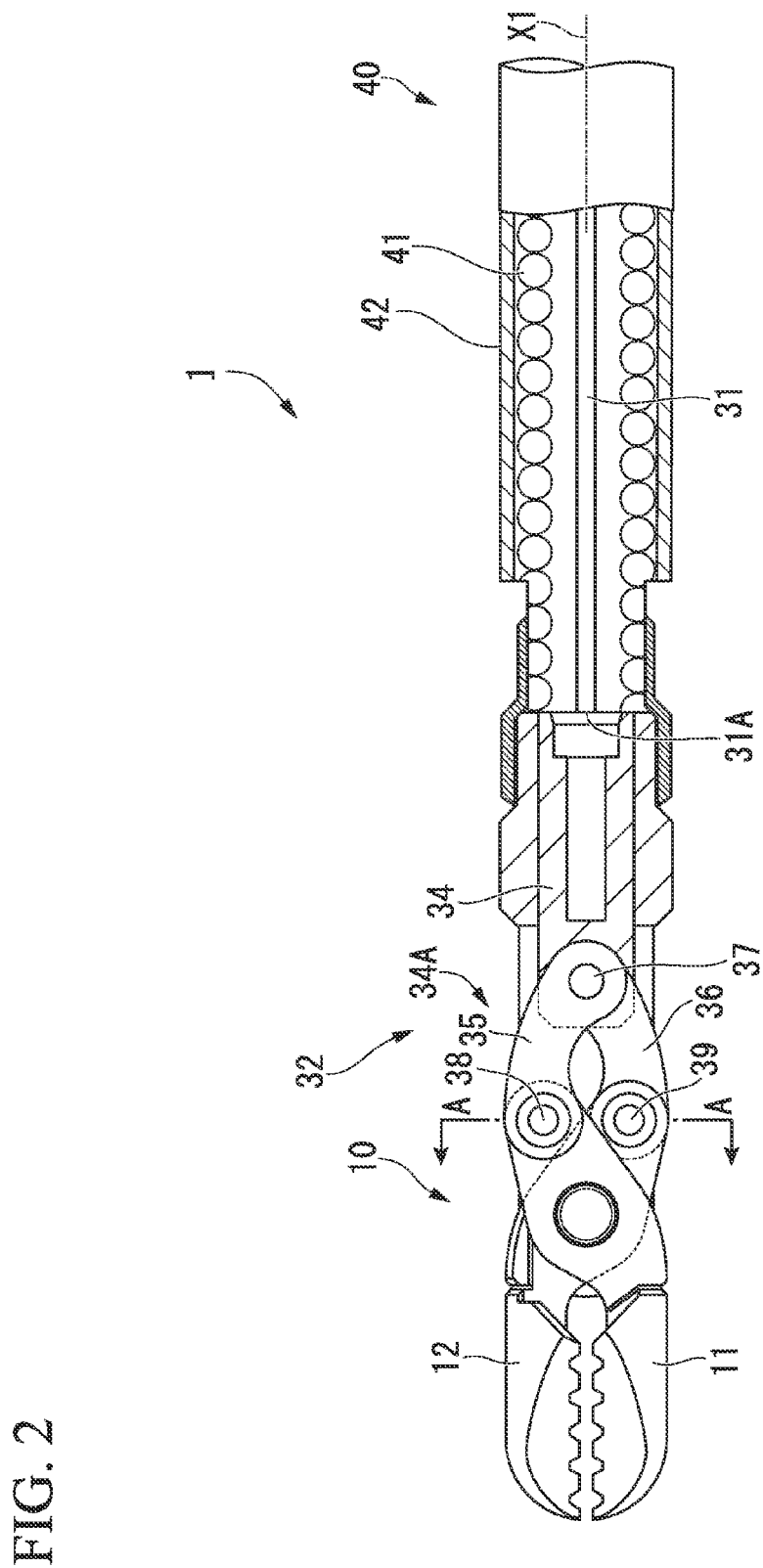
FIG. 2 is a diagram of the vicinity of a treatment part of a treatment tool for endoscope according to a first embodiment of the invention, with a cover removed.

FIG. 2 is a diagram of the vicinity of the treatment part 10 of the treatment tool 1 with the cover 14 removed. As shown in FIG. 2, the connection part 30 includes an operation wire 31, and a link mechanism 32 attached to the distal end of the operation wire 31. The operation wire 31 has a publicly known configuration. A first end part 31A on the distal-end side of the operation wire 31 is connected to the link mechanism 32, and a second end part 31B on the proximal-end side (see FIG. 1) is connected to the slider 22 of the operation part 20.

The link mechanism 32 includes a connection member 34 attached at the distal end of the operation wire 31, and a pair of link members consisted of a first link member 35 and a second link member 36 that connect the connection member 34 to the pair of forceps members 11 and 12.

One link rotation member 34A is provided on the distal-end side of the connection member 34. The proximal ends (second end parts) of the first link member 35 and the second link member 36 are rotatably connected by pins 37 to the link rotation member 34A. The distal-end sides (first end parts) of the link members 35 and 36 are rotatably connected via rotation axis members 38 and 39 respectively to the proximal-end parts of the forceps members 11 and 12 respectively.

Figure 3:
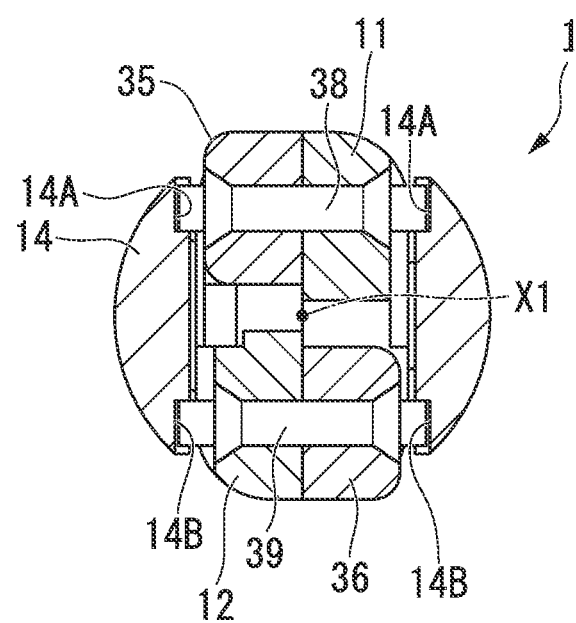
FIG. 3 is a cross-sectional diagram along the line A-A of FIG. 2.

FIG. 3 is a cross-sectional diagram along the line A-A of FIG. 2. In FIG. 3, the cover 14 is shown. As shown in FIG. 3, the length of each of the rotation axis members 38 and 39 is greater than the total thickness of the connected forceps members and link members. The rotation axis members 38 and 39 are inserted into the forceps members and link members such that their end parts protrude towards the cover 14.

Grooves (restricting parts) 14A and 14B are provided in the inner face of the cover 14 opposite the forceps members 11 and 12 and the link members 35 and 36, and have width dimension enough to enable the rotation axis members 38 and 39 to be accommodated in them. Both end parts of the protruding rotation axis members 38 and 39 are respectively accommodated in the grooves 14A and 14B, and engage with them.

The groove 14A is formed of opening only in a direction of separating from the axis X1 of the operation wire 31, and does not extend further to the groove 14B side than the rotation axis member 38. Similarly, the groove 14B is formed of opening only in a direction of separating from the axis X1 of the operation wire 31, and does not extend further to the groove 14A side than the rotation axis member 39.

Since the grooves 14A and 14B have the shapes described above, the rotation axis members 38 and 39 can move from the state shown in FIG. 3 to the direction of separating from the axis X1. However, since they are restricted by the grooves 14A and 14B, the rotation axis members 38 and 39 cannot completely move in the direction of approaching the axis X1, and can only move a slight distance.

Figure 4:
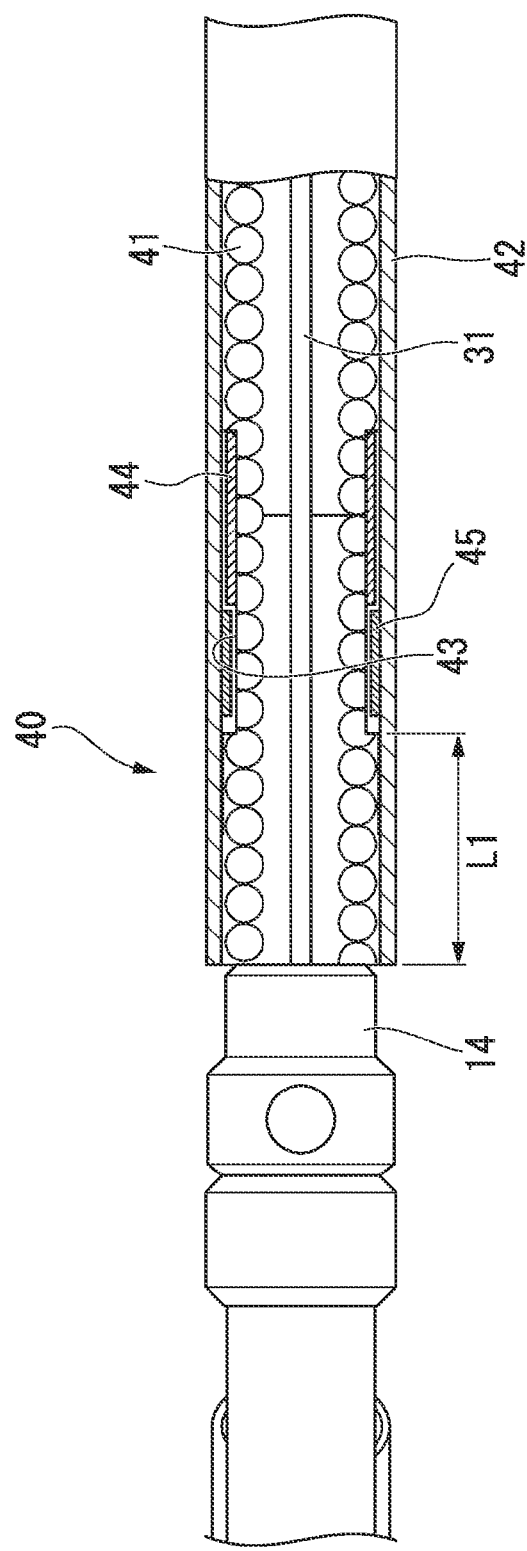
FIG. 4 is a partial cross-sectional diagram of a distal-end side of an insertion part of a treatment tool for endoscope according to a first embodiment of the invention.
Figure 5:
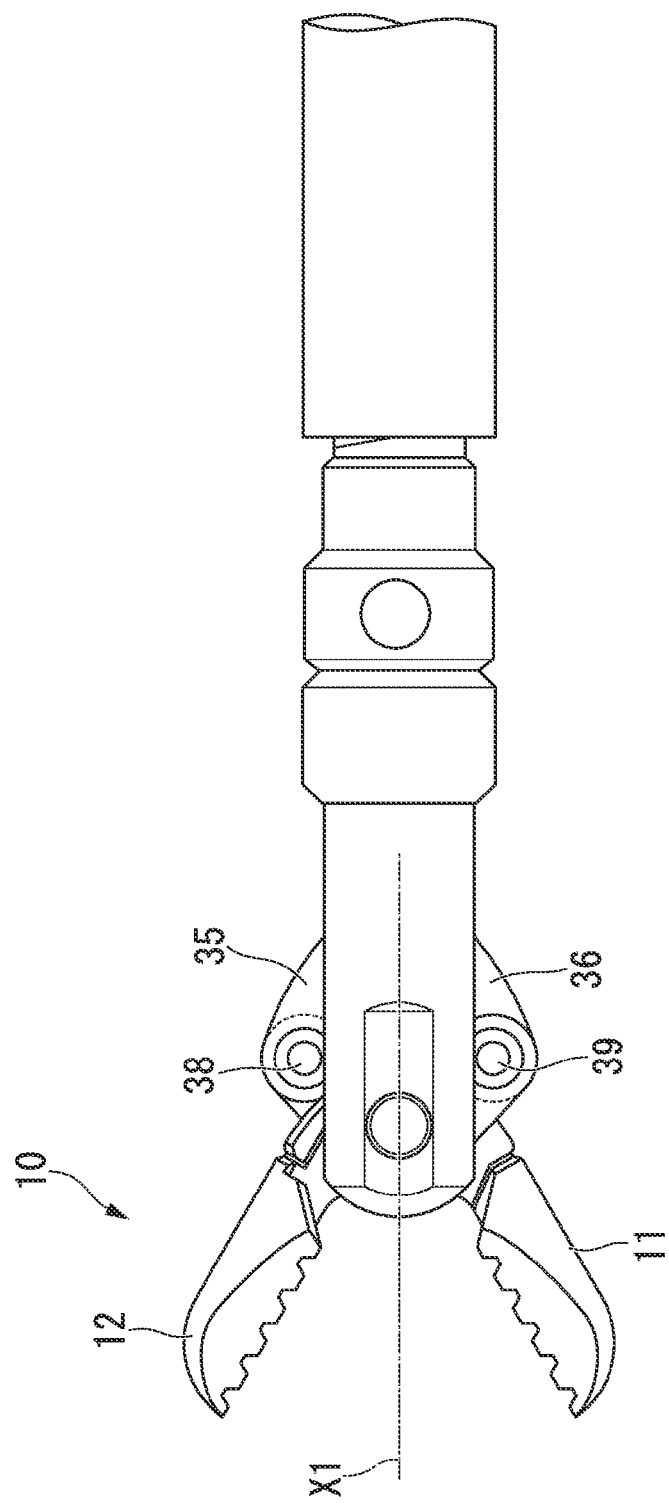
FIG. 5 is a diagram of one operation when using a treatment tool for endoscope according to a first embodiment of the invention.

FIG. 4 is a partial cross-sectional diagram of the distal-end side of the insertion part 40. As shown in FIG. 4, the insertion part 40 includes a coil sheath 41 which the operation wire 31 is inserted into, and a tube sheath 42 which the coil sheath 41 has been inserted into.

Various types of publicly known members can suitably be used as the coil sheath 41. The cover 14 is attached to the distal end of the coil sheath 41, and the proximal end of the cover 14 id secured to the main unit 21 of the operation part 20 (see FIG. 1).

The outer peripheral face of the coil sheath 41 is cut away at a position on the proximal-end side no more than a predetermined length L1 from the distal end, forming a small-diameter part 43 with a small external diameter. The coil sheath 41 is divided into two pieces at the small-diameter part 43. The coil sheath 41 is then brazed or the like via a connection ring 44 attached to the small-diameter part 43, forming a single-piece coil sheath.

Various types of publicly known members made from resin and the like can suitably be used as the tube sheath 42. As shown in FIG. 1, the proximal end of the tube sheath 42 is inserted into the opening provided in the distal end of the main unit 21, and can rotate relative to the main unit 21.

A ring member (advancement/retraction-suppressing member) 45 which is fitted into the small-diameter part 43 of the coil sheath 41 is pressed into the tube sheath 42. The inner diameter of the ring member 45 is set such that, when in the pressed-in state, it is smaller than the basic outer diameter of the coil sheath 41 (the outer diameter of the part other than the small-diameter part 43) and the outer diameter of the connection ring 44. The inner diameter of the ring member 45 is larger than the outer diameter of the small-diameter part 43, so that clearance is maintained between them.

Having the configuration described above, the coil sheath 41 and the tube sheath 42 are formed so that they can rotate relatively about the axis and cannot practically move relatively in the axis direction. To realize the configuration described above, one coil sheath with a small-diameter part 43 is cut at the small-diameter part 43 and divided into two pieces. With the ring member 45 fitted to the small-diameter part of the coil sheath at the distal-end side, the connection ring 44 is used to connect the cut pieces of the coil sheath into one piece. The coil sheath 41 with the ring member 45 attached thereto is then inserted into the tube sheath 42, and the ring member 45 is pressed into the tube sheath 42, thereby obtaining the insertion part 40 of the treatment tool 1.

The predetermined length L1 can be set as appropriate. However, in regard to the insertion part 40 between the connection member 34 of the connection part 30 and the ring member 45, to practically shorten the hard length (explained below) on the distal-end side of the treatment tool 1, the length is preferably one that enables it to flexibly deform sufficiently, for example, more than 20 millimeters (mm).

An operation when using the treatment tool 1 having the configuration described above will be explained.

Firstly, an endoscope (not shown) is inserted into the body of a patient, and a distal end of the endoscope is advanced until it is near a body cavity tissue (target tissue) that is the treatment target.

The slider 22 is retracted with respect to the main unit 21 of the operation part 20. The insertion part 40 is then inserted into a forceps channel of the endoscope while the pair of forceps members 11 and 12 are in a closed state. The treatment part 10 protrudes from the distal end of the forceps channel. At this time, the treatment part 10 at the distal end of the treatment tool 1 and one part of the connection part 30 covered by the cover 14 are separated by no more than the predetermined length L1 from the point where the ring member 45 of the insertion part 40 is provided. Therefore, the section of the insertion part 40 between the treatment part 10 at the distal end of the treatment tool 1 and one part of the connection part 30 covered by the cover 14, and the point where the ring member 45 of the insertion part 40 is provided, is flexible. As a result, even if the endoscope meanders or the like inside the body cavity, this section flexibly deforms well and follows the shape of the endoscope. This makes it easier to insert the treatment tool 1 into the forceps channel of the endoscope.

In performing treatment, the slider 22 is advanced with respect to the main part 21. The operation wire 31 connected to the slider 22 consequently advances with respect to the coil sheath 41. As described above, since the forceps rotation member 13 is supported by the cover 14 attached to the coil sheath 41, the first forceps member 11 and the second forceps member 12 each rotate around the forceps rotation member 13 secured to the insertion part 40. As a result, the treatment part 10 opens in the manner shown in FIG. 5.

When the treatment part 10 opens, the proximal ends of the first forceps member 11 and the second forceps member 12 protrude from the cover 14. In conjunction therewith, the rotation axis members 38 and 39 inserted into the proximal ends of the respective forceps members 11 and 12 also move to positions where they do not overlap with the cover 14 in the side view shown in FIG. 5. The grooves 14A and 14B, which the rotation axis members 38 and 39 are engaged with, open in directions of separating from the axis line X1 of the operation wire 31. The pair of forceps members 11 and 12 can therefore open smoothly, without any obstruction of the above-described movements of the rotation axis members and the proximal ends of the forceps members.

On the other hand, since the grooves 14A and 14B do not extend in directions of approaching the axis X1, the rotation axis members 38 and 39 do not move in directions of approaching the axis X1 while the treatment part 10 is opening and closing.

A user carries out the desired treatment to the target tissue while opening and closing the pair of forceps members 11 and 12 of the treatment part 10 by advancing and retracting the slider 22. As necessary, the user can adjust the positional relationship between the target tissue and the open/closed faces of the pair of forceps members 11 and 12 by rotating the main part 21 around the axis to rotate the treatment part 10.

According to the treatment tool 1 of this embodiment, the rotation axis members 38 and 39, which are the points where the forceps members 11 and 12 connect to the link members 35 and 36, engage respectively with the grooves 14A and 14B provided in the cover 14. As a result, the movement of the rotation axis members 38 and 39 in directions of approaching the axis X1 of the operation wire 31 is thus restricted. As a result, the forceps rotation axis 13, one of the rotation axis members 38 and 39, and the link rotation member 34A move so that they are arranged in a single straight line. It is therefore possible to prevent occurrence of the state where it is difficult to open and close the pair of forceps members as described above, and thereby to ensure that they open and close stably.

The hard treatment part 10 and one part of the connection part 30 are separated by the predetermined length L1 from the ring member 45 that connects the coil sheath 41 to the tube sheath 42 on the insertion part 40 so that they can rotate relatively. Therefore, when the hard treatment part 10 and the like are near the ring member 45, the hard length of the distal-end side of the treatment tool 1, which is the sum of the sizes of the above parts in the directions of their rotation axes, is practically shortened. This obtains a treatment tool with superior insertability into the endoscope.

Subsequently, a second embodiment of the invention will be explained with reference to FIGS. 6 to 10. In a treatment tool 51 of this embodiment, the structures of the link mechanism and the restricting part are different from those of the first embodiment.

In the explanation that follows, constituent parts that are common to the treatment tool of the embodiment already explained above are designated with like reference numerals, and are not repetitiously explained.

Figure 6:
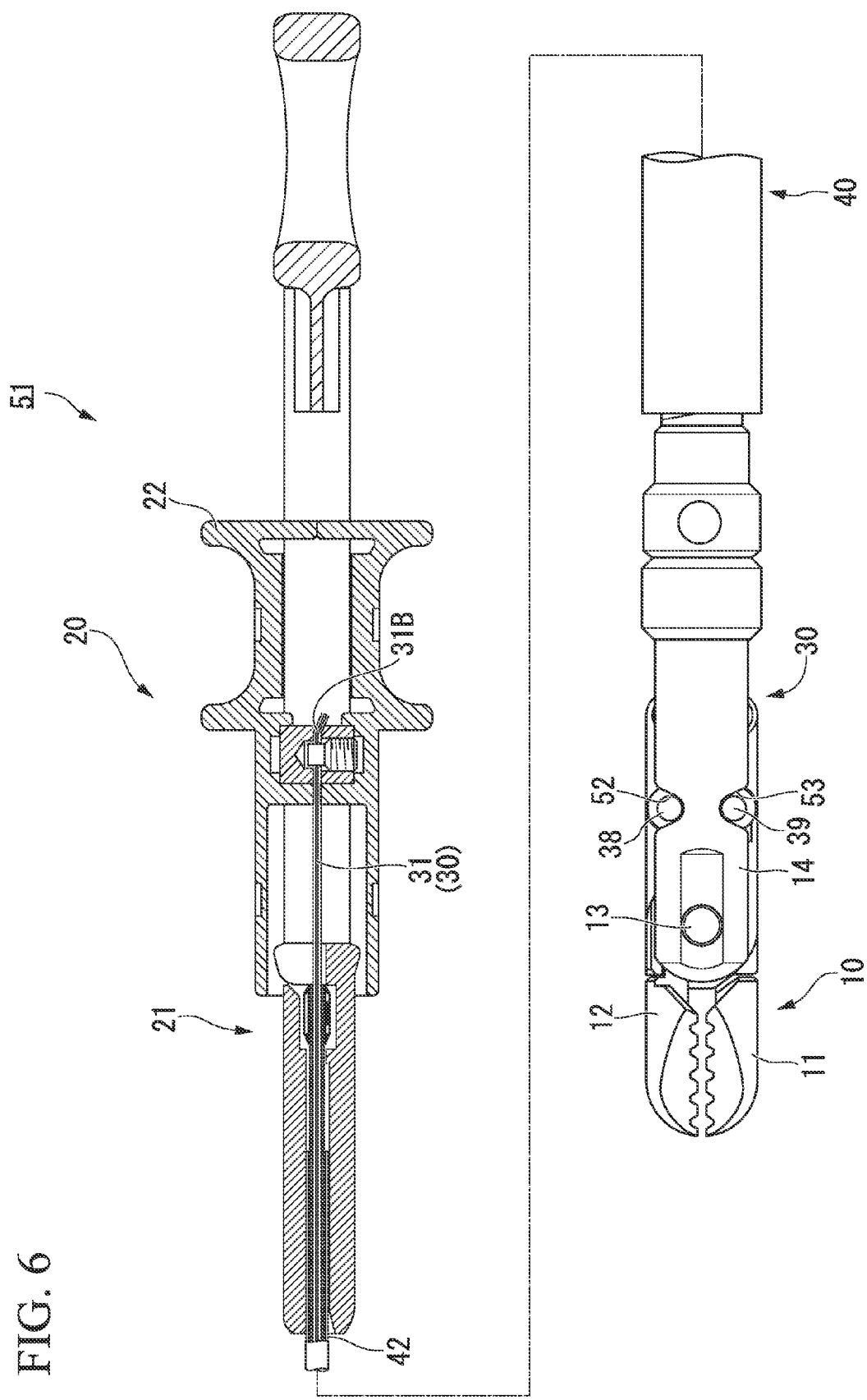
FIG. 6 is an overall diagram of a treatment tool for endoscope according to a second embodiment of the invention.

FIG. 6 is an overall diagram of a treatment tool 51. Instead of the grooves 14A and 14B, notches 52 and 53 are formed in the cover member 14 as restricting parts. These notches 52 and 53 will be explained in greater detail later.

Figure 7:
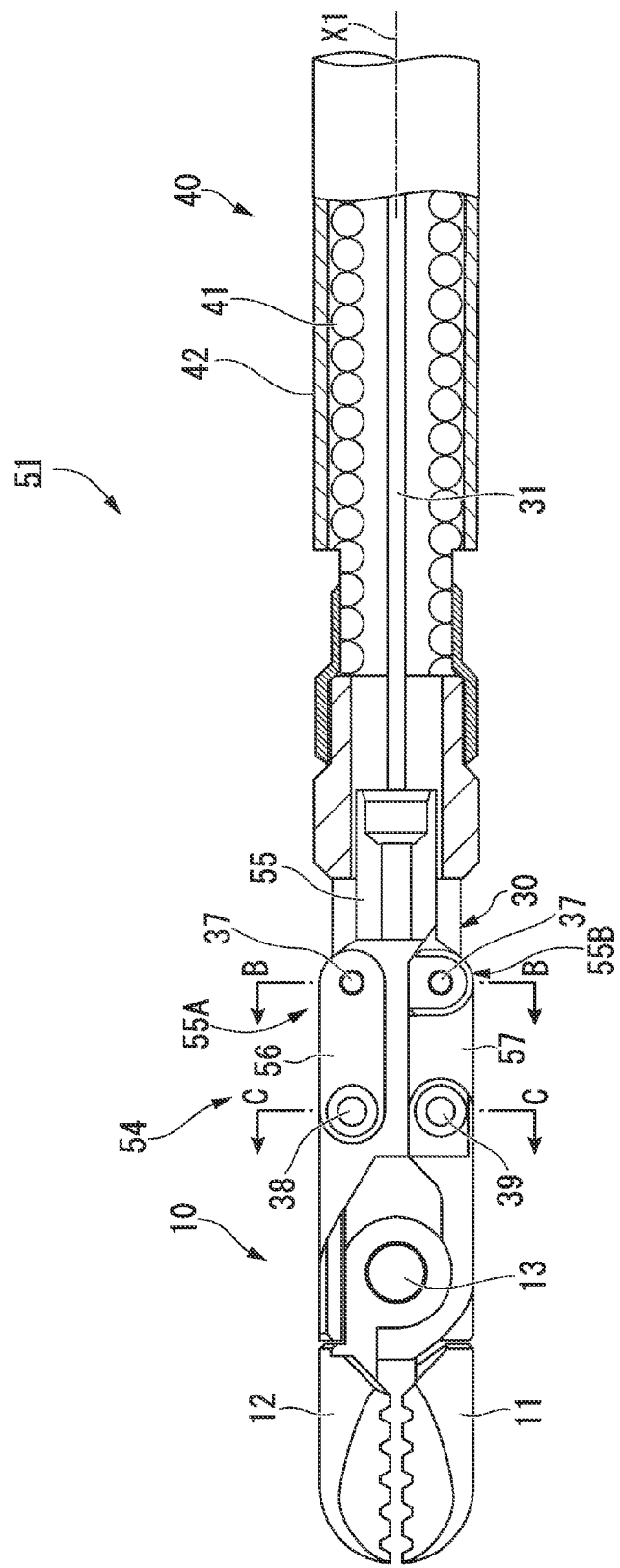
FIG. 7 is a diagram of the vicinity of a treatment part of a treatment tool for endoscope according to a second embodiment of the invention, with a cover removed.

FIG. 7 is a diagram of the vicinity of the treatment part 10 of the treatment tool 51 with the cover 14 removed. A link mechanism 54 of the treatment tool 51 includes a connection member 55 instead of the connection member 34, and includes a first link member 56 and a second link member 57 instead of the first link member 35 and the second link member 36.

The connection member 55 has two link rotation members 55A and 55B. The first link member 56 and the second link member 57 are formed in substantially oblong shapes extending in their own long directions. A proximal-end part of the first link member 56 is rotatably connected via a pin 37 to the link rotation member 55A, and a proximal-end part of the second link member 57 is rotatably connected via a pin 37 to the link rotation member 55B.

The link rotation members 55A and 55B are separated by equal distances (including substantially equal distances) from the axis X1 of the operation wire 31, and face each other from either side of the axis X1. The two pins 37 are disposed so that their axes are parallel (including substantially parallel; hereinafter likewise), and the two link rotation members 55A and 55B are disposed parallel with each other.

When the pair of forceps members 11 and 12 are in the closed state, the link members 56 and 57 are parallel to each other and their long directions are parallel with the axis X1.

Figure 8:
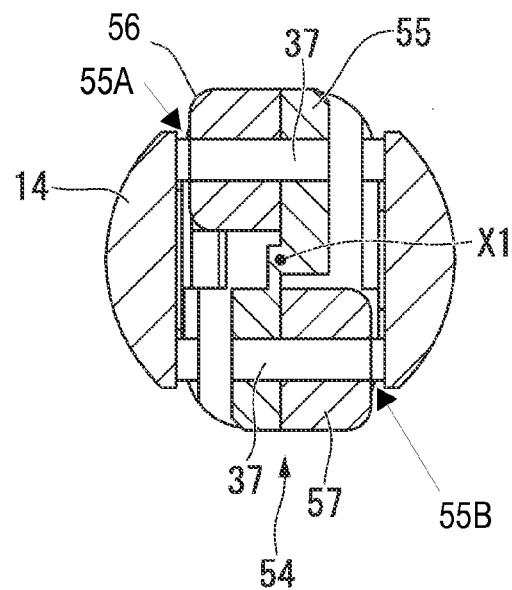
FIG. 8 is a cross-sectional diagram along the line B-B of FIG. 7.

FIG. 8 is a cross-sectional diagram along the line B-B of FIG. 7, and shows the cover 14 as with FIG. 3. As shown in FIG. 8, the face of the connection member 55 that is orthogonal to the axis line X1 is crank-shaped, such that the point where the link rotation member 55A is formed and the point where the link rotation member 55B is formed are alternately on either side of the axis X1. Therefore, the maximum thickness of the link mechanism 54 is a value near to the sum of the thickness of the connection member 55 and the thicknesses of the link members 56 and 57 in the either link rotation members 55A and 55B, and is thus suppressed to the thickness of two members.

Figure 9:
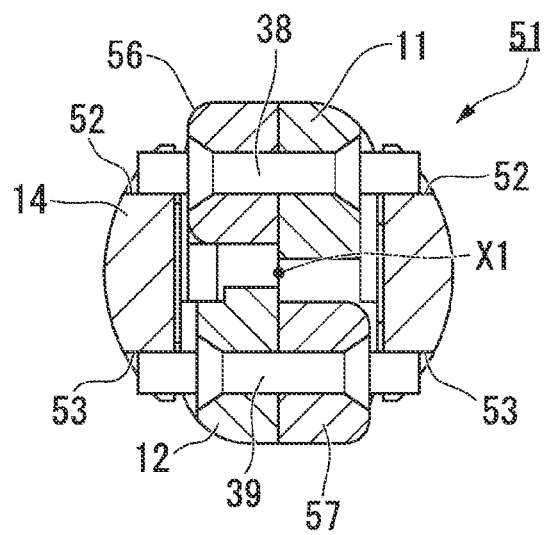
FIG. 9 is a cross-sectional diagram along the line C-C of FIG. 7.

FIG. 9 is a cross-sectional diagram along the line C-C of FIG. 7, and also shows the cover 14. As shown in FIG. 9, the notches 52 and 53 formed in the cover 14 penetrate in the extension directions of the rotation axis members 38 and 39. The ends of the rotation axis members 38 and 39 engage with the notches 52 and 53 respectively. The shapes of the notches 52 and 53 are similar to those of the grooves 14A and 14B of the first embodiment, in that they open in the direction of separating from the axis X1, and that, when the pair of forceps members 11 and 12 are in the closed state, each notch does not extend towards the other any further than the positions where the rotation axis members 38 and 39 engage with them. However, in the side view shown in FIG. 6, the widths of the notches 52 and 53 (their dimensions in the directions the axis X1 extending) gradually increase as they lead away from the axis X1. This feature differs from the grooves 14A and 14B.

Figure 10:
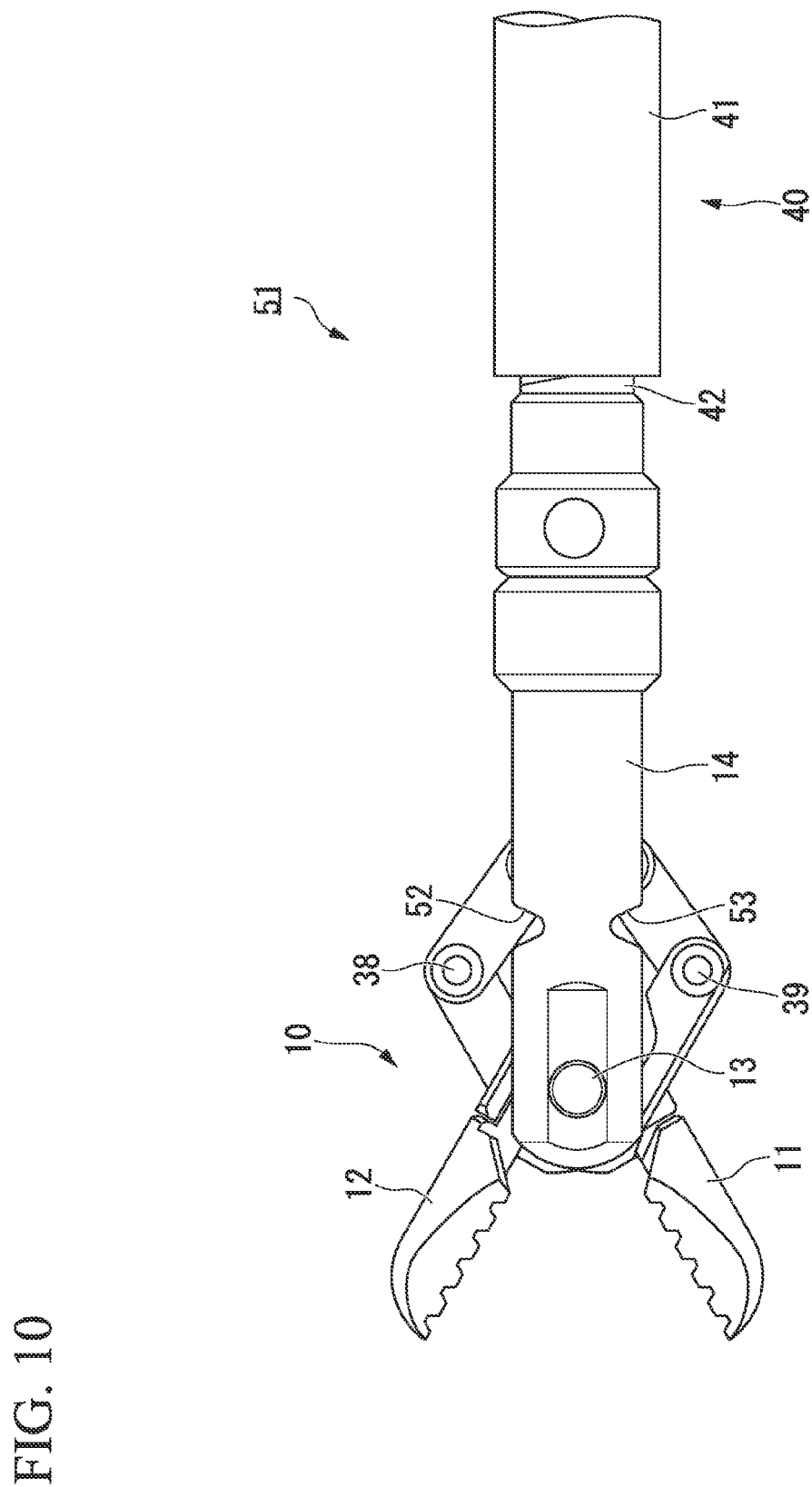
FIG. 10 is a diagram of one operation when using a treatment tool for endoscope according to a second embodiment of the invention.

In the treatment tool 51 configured as described above, when the operation wire 31 is advanced by operating the operation part 20, as shown in FIG. 10, the first forceps member 11 and the second forceps member 12 of the treatment part 10 rotate around the forceps rotation member 13 and open. The movement of the rotation axis members 38 and 39 in the direction of approaching the axis X1 is favourably restricted when they engage with the notches 52 and 53 formed in the cover 14.

As with the treatment tool 1 of the first embodiment, the treatment tool 51 of this embodiment can ensure that the treatment part opens and closes stably. In the link mechanism 54 of the treatment tool 51, when the pair of forceps members 11 and 12 is in the closed state, the link members 56 and 57 are parallel with the axis X1 of the operation wire 31. The forceps rotation axes, one of the rotation axis members, and the link rotation members consequently move such that they are in a single straight line, and a state where there is difficulty in opening and closing the pair of forceps members is more likely to occur than with the treatment tool 1. However, since the notches 52 and 53 are provided in the cover 14 and function as restricting parts, that state can favourably be suppressed.

As the notches 52 and 53 lead away from the axis X1, they gradually widen and the widths of their open sections reach their maximum.

Since the operation wire 31 advances when the pair of forceps members 11 and 12 are opened, the rotation axis members 38 and 39 lead away from the axis X1 and, as shown in FIG. 10, they slight advance toward the cover 14. Thus the rotation axis members 38 and 39 move forwards and backwards in the axis X1 direction as the forceps members open and close. However, since the open sections of the notches 52 and 53 have large widths, the rotation axis members and the notches engage with and disengage from each other smoothly, and the treatment part opens and closed smoothly.

The connection member 55 also includes the two link rotation members 55A and 55B which are set away from the axis X1 of the operation wire 31. Moreover, the first link member 56 and the second link member 57 are respectively connected to the two link rotation members 55A and 55B. Therefore, the extension-direction thicknesses of the link rotation members 55A and 55B at the connection points between the connection member 55 and the link members 56 and 57 become the thickness of two members, which is the sum of the connection member 55 and one of the link members 56 and 57. As a result, the distal-end side region including the treatment part is made even narrower than in the configuration of the treatment tool 1, where the two link members are connected to a single link rotation member.

While preferred embodiments of the invention have been described and illustrated above, the technical field of the invention is not limited to these embodiments. The constituent elements of the embodiments can be combined and changed, modified in various ways, and deleted, without departing from the spirit or scope of the present invention.

For example, when the notches of the second embodiment are used as restricting parts, while increasing the lengths of the rotation axis members makes them engage more reliably with the notches, parts of the rotation axis members protrude from the outer shape of the cover 14. In such a case, parts of the ends of the rotation axis members can be subjected to a process such a cutting, so as to eliminate the sections protruding from the outer shape of the cover member 14. This enables the treatment tool to smoothly advance into and retract from the endoscope channel and the body cavity, and favourably suppresses damage to the body cavity tissue and the like.

The configuration of the treatment tool of this invention can also be applied in a monopolar or bipolar high-frequency treatment tool for carrying out treatment by passing an electric current through a treatment part.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A treatment tool for endoscope, used by being inserted via an endoscope into a body cavity, comprising:
   a pair of forceps members supported by a forceps rotation member so as to be rotatable relative to each other;
   an operation part that performs an open-close operation of the pair of forceps members;
   an operation wire that connects the pair of forceps members and the operation part;
   an insertion part which the operation wire is inserted into;
   a cover member that secures the forceps rotation member to the insertion part;
   a connection member including a link rotation member, and provided at a distal-end part of the operation wire; and
   a pair of link members, in which first end parts of each of the link members are rotatably connected via respective rotation axis members to a proximal-end part of each of the pair of forceps members, and second end parts of each of the link members are rotatably connected to the link rotation member,
   wherein the connection member includes two of the link rotation members and axes of the link rotation members are parallel with each other in a direction separating from an axis of the operation wire, a cross-sectional shape of the connection member which is orthogonal to the axis of the operation wire is crank-shaped such that a first link rotation member which is connected to a proximal end part of the first link member and a second link rotation member which is connected to a proximal end part of the second link member are formed alternatively on either side of the axis of the operation wire,
   second end parts of the pair of link members are rotatably connected to each of the two link rotation members, and when the pair of forceps members are in a closed state, the link members are parallel to each other, and
   the cover member includes restricting parts formed as grooves or notches which open in a direction separating from the axis of the operation wire, and formed such that, in a state that the pair of forceps members are closed and the rotation axis members are positioned so as to separate from the axis of the operation wire, by engaging with end parts of the rotation axis members, the restricting parts restrict the movement of the rotation axis members in a direction approaching to the axis of the operation wire.

2. The treatment tool according to claim 1, wherein a notch is formed in each of the cover members so as to penetrate in an extension direction of each of the rotation axis members, and both ends of the rotation axis members engage with the notches respectively.

3. The treatment tool according to claim 1, wherein dimensions of the notches in a direction of the axis of the operation wire is formed gradually increasing with increasing distance from the axis of the operation wire.

* * * * *